(12) United States Patent
Chang et al.

(10) Patent No.: US 7,758,803 B2
(45) Date of Patent: Jul. 20, 2010

(54) RESORBABLE MACROPOROUS BIOACTIVE GLASS SCAFFOLD AND METHOD OF MANUFACTURE

(76) Inventors: Jiang Chang, 1295 Dingxi Road, Shanghai, CN (CN) 200050; Weiming Gu, 1295 Dingxi Road, Shanghai, CN (CN) 200050; Jipin Zhong, 3636 NW. 68th La., Gainesville, FL (US) 32653

( * ) Notice: Subject to any disclaimer, the term of this patent is extended or adjusted under 35 U.S.C. 154(b) by 1000 days.

(21) Appl. No.: 11/329,469

(22) Filed: Jan. 11, 2006

(65) Prior Publication Data
US 2007/0162151 A1 Jul. 12, 2007

(51) Int. Cl.
*B28B 1/14* (2006.01)
(52) U.S. Cl. .................. 264/621; 264/667
(58) Field of Classification Search ........... 264/621, 264/667
See application file for complete search history.

(56) References Cited

U.S. PATENT DOCUMENTS

| | | | |
|---|---|---|---|
| 5,977,204 A * | 11/1999 | Boyan et al. | 523/113 |
| 6,054,400 A * | 4/2000 | Brink et al. | 501/63 |
| 6,344,496 B1 * | 2/2002 | Niederauer et al. | 523/113 |
| 6,767,854 B2 * | 7/2004 | Berger et al. | 501/10 |
| 2003/0219466 A1 * | 11/2003 | Kumta et al. | 424/423 |
| 2004/0002770 A1 | 1/2004 | King et al. | |
| 2004/0043053 A1 * | 3/2004 | Yu et al. | 424/426 |
| 2004/0228905 A1 * | 11/2004 | Greenspan et al. | 424/445 |
| 2006/0292198 A1 * | 12/2006 | Dalal et al. | 424/422 |
| 2007/0224286 A1 * | 9/2007 | Kutty et al. | 424/602 |
| 2007/0275021 A1 * | 11/2007 | Lee et al. | 424/401 |
| 2008/0038534 A1 * | 2/2008 | Zenati et al. | 428/312.6 |
| 2008/0060382 A1 * | 3/2008 | Rake et al. | 65/21.2 |
| 2008/0066495 A1 * | 3/2008 | Moimas et al. | 65/17.1 |

* cited by examiner

*Primary Examiner*—Steven P Griffin
*Assistant Examiner*—Russell J Kemmerle, III
(74) *Attorney, Agent, or Firm*—Thomas C. Saitta

(57) ABSTRACT

A resorbable, macroporous bioactive glass scaffold comprising approximately 24-45% CaO, 34-50% $SiO_2$, 0-25% $Na_2O$, 5-17% $P_2O_5$, 0-5% MgO and 0-1% $CaF_2$ by mass percent, produced by mixing with pore forming agents and specified heat treatments.

3 Claims, 4 Drawing Sheets

RESORBABLE MACROPOROUS BIOACTIVE GLASS SCAFFOLD AND METHOD OF MANUFACTURE

TECHNICAL AREA

This invention relates to the area of biomaterials involving resorbable or degradable, macroporous bioactive glass material which can be used either for the restoration of hard tissues or as the tissue engineering scaffold, as well as preparation methods for such materials.

BACKGROUND TECHNOLOGY

There has been a history of over 30 years in research on bioactive glass since 1971 when Dr. Larry Hench reported that such glass could bond together with bone tissues for the first time. Also, such glass material has been used for restoration of bone defects in clinical practice for over ten years, and such clinical applications have proven successful in that this glass can bring along not only the benefit of osteoconduction, but also the bioactivity to stimulate the growth of bone tissues. Many recent studies have revealed that the degradation products of bioactive glass can enhance the generation of growth factors, facilitate cellular proliferation and activate gene expression of osteoblasts. Moreover, bioactive glass is the only synthetic biomaterial so far that can both bond with bone tissues and soft tissues. These unique features of this glass have created a great potential for its clinical application as a type of medical device, and thereby, attracted great attention from both academia and the industrial sector. Despite its excellent biocompatibility and bioactivity, bioactive glass can be now produced only in a granular form for clinical application. For restoration of bone defects, macroporous and block scaffold materials with a particular mechanical strength are often needed to fill in and restore such defects. Even in the field of tissue engineering, which receives world-wide attention and evolves rapidly, macroporous bioactive scaffold materials are similarly demanded to serve as cell carriers.

Research studies in the past have suggested that besides the composition of the material, its structure can directly influence its clinical applications as well. The macroporous and block scaffold materials with bioactivity whose pore sizes are in the range of 50-500 microns are most suitable to be used as materials either for the restoration of bone defects, or as cell scaffolds. Any macroporous biomaterial having a pore size within the said range can bring benefits to the housing and migration of cells or tissue in-growth, as well as to the bonding of such a material to living tissues, thereby achieving the goals of repairing defects in human tissues and reconstructing such tissues more effectively.

Moreover, the subject of the biomaterials that are both resorbable and macroporous has now become an integral part of tissue engineering studies that have been rapidly developed in recent years, where scaffolds made of such macroporous materials can be adopted to serve as cell carriers so that cells can grow in the matrix materials and constitute the living tissues that contain genetic information of the cell bodies, and such tissues can be in turn, implanted into human bodies to restore tissues and organs with defects. Therefore, resorbable, macroporous bioactive glass scaffold materials possess wide-ranging potential for their applications as cell scaffolds either for restoration of defects in hard tissues, or for the purpose of in vitro culture of bone tissues.

U.S. Pat. Nos. 5,676,720 and 5,811,302 to Ducheyne, et al, teach a hot-pressing approach using inorganic salts such as calcium carbonate and sodium bicarbonate as the pore-forming agents to prepare and manufacture macroporous bioactive glass scaffolds which have the compositions of $CaO-SiO_2-Na_2O-P_2O_5$, and which are designed to function as the cell scaffolds used for in vitro culture of bone tissues. Nevertheless, this hot-pressing approach if adopted would entail high production costs, and furthermore, controlling the composition of the finished products is difficult because the composition will be affected by the remnants that result after sintering the inorganic salts used as pore-forming agents. Additionally, Yuan, et al. have adopted oxydol as a foaming agent to prepare and manufacture 45S5 bioactive glass scaffolds under a temperature of 1000° C., with the scaffolds produced in this way being bioactivity and having the ability to bond together with bone tissues (J.Biomed.Mater.Res; 58:270-267,2001). But according to our testing results, the glasses will become substantially crystallized and their resorbability/degradability will decrease if they are sintered under a temperature of 1000° C. In addition, it is quite difficult to control the pore size and pore number of the materials when oxydol is used as the foaming agent.

Mechanical strength is also an important factor for performance of macroporous bioactive glass scaffold materials, and relevant studies have suggested that any compressive strength below 1 MPa would result in the poor applicability of these scaffold materials, and thus, in the course of applying them either as cell scaffolds or for the purpose of restoration of bone injuries, such materials would be very prone to breakage or damage, therefore limiting the effectiveness of their application. So far, no report on the compressive strength standard data of macroporous bioactive glass scaffolds has been found in previous patent and published documents and as a result, gives rise to the purpose of this invention to determine proper technical control measures to keep the compressive strength of the manufactured bioactive glass scaffold within a certain range to meet the requirements of various applications.

SUMMARY OF THE INVENTION

The purpose of this invention is to develop, through the optimization of technology and process, a new type of macroporous bioactive glass scaffold with interconnected pores, which features excellent bioactivity, biodegradability, controllable pore size and porosity. Such a scaffold would serve as a means to repair defects in hard tissues and be applied in the in vitro culture of bone tissues, and its strength can be maintained within a range of 1-16 MPa in order to meet demands arising from the development of the new-generation biological materials and their clinical applications.

This invention has been designed to use glass powders as raw material, into which organic pore forming agents will be added, and the mixture will be processed by either the dry pressing molding method or gelation-casting method, and then the resulting products will be obtained by sintering under appropriate temperatures. In this way, a macroporous bioactive glass scaffold can be obtained with various porosities, pore sizes and pore structures, as well as different degrees of compressive strength and degradability. The chemical composition of such scaffolds shall be expressed as CaO 24-45%, $SiO_2$ 34-50%, $Na_2O$ 0-25%, $P_2O_5$ 5-17%, MgO 0-5 and $CaF_2$ 0-1%. Additionally, the approaches provided in this invention can be adopted to prepare the said scaffold in different shapes. The crystallizations of calcium phosphate and/or calcium silicate can be formed inside the bioactive glass scaffolds by way of technical control, whereby both the degradability and mechanical strength of the macroporous materials can be controlled as demanded.

As designed in this invention, the macroporous bioactive glass scaffold materials exhibit excellent biological activity, and can release soluble silicon ions with precipitation of bone-like hydroxyl-apatite crystallites on their surface in just a few hours after being immersed into simulated body fluids (SBF). In addition, the macroporous bioactive glass in this invention is resorbable, as shown by in vitro solubility experiments, and such glass demonstrates a degradation rate of approximately 2-30% after being immersed in simulated body fluids (SBF) for 5 days. As such, it can be concluded that the macroporous bioactive glass scaffold materials in this invention do not only have desirable biointerfaces and chemical characteristics, but also demonstrate excellent resorbability/degradability.

Another feature of this invention is manifested in controlling technical conditions to create materials that can have both a relatively higher porosity (40-80%) with suitable pore size (50-600 microns), and exhibit a proper mechanical strength (with the compressive strength at 1-16 MPa).

DETAILED DESCRIPTION OF THE INVENTION

Figure 1:
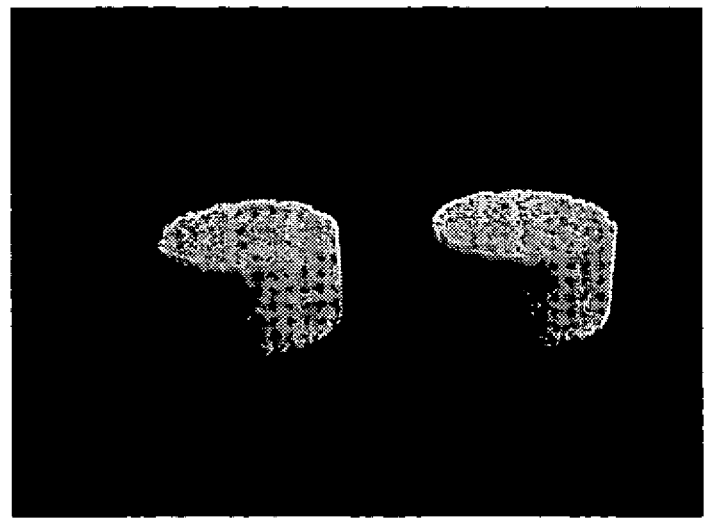
FIG. 1 is a photograph of the prepared macroporous bioactive glass.

The implementation of this invention is detailed as below:

1. Preparation of Materials:

The bioactive glass powder in this invention is prepared using the melting method. The inorganic materials applied in the present invention are all of analytical purity. Specifically, these chemical reagents are weighed and evenly mixed in line with requirements for proper composition results, and then melted in temperatures ranging from 1380° C. to 1480° C. to produce glass powders with a granularity varying from 40 to 300 µam after cooling, crushing and sieving procedures. Furthermore, such glass powders are then used as the main raw material to prepare a variety of the macroporous bioactive glass scaffold substances by way of different processing technologies. The pore forming agents specified in the present invention can be organic or polymer materials such as polyethylene glycol, polyvinyl alcohol, paraffin and polystyrene-divinylbenzene, etc., whose granularity can fall in the range of 50-600 microns. Thus, the pore forming agent within a certain granularity range (20-70% in mass percent) can be blended with the said bioactive glass powders and the resulting mixture can be molded by adopting either of the following two approaches:

First, the dry pressing molding approach, in which 1-5% polyvinyl alcohol (concentration at 5-10%) is added to the said mixture as the adhesive, which is stirred, and then dry-pressed into a steel mold (pressure at 2-20 Mpa) to produce a pellet of the macroporous material, which is then sintered (temperature at 750-900° C.) for 1-5 hours to obtain final product.

Second, the gelation-casting approach, in which an aqueous solution is prepared as per the following mass percent concentrations: 20% acrylamide, 2% N, N'-methylene-bis-acrylamide cross-linking agents and 5-10% polyacrylic acid dispersant agents. Next, the aforementioned mixture and the aqueous solution (volume percent at 30-60%) is combined and mixed, and ammonium persulfate (1-5% in mass percent) and N, N, N', N'-tetramethyl ethylene diamine (1-5% in mass percent) is added. Then, the above-mentioned materials are stirred to produce a slurry with fine fluidity and homogeneity, which is then poured into plastic or plaster molds for gelation-casting. Later the cross-linking reaction of monomers is induced under temperatures ranging from 30° C. to 80° C. for 1-10 hours, and pellets of the macroporous material are obtained after a few hours of drying at 100° C. The pellets are processed first at the temperature of 400° C. to remove organics, and then sintered at 750-900° C. to obtain the macroporous material of the present invention.

2. Performance Evaluation 2.1. The Mechanical Strength of the Macroporous Material:

An array of samples obtained in this invention was tested for their respective compressive strengths using the Autograph AG-I Shimadzu Computer-Controlled Precision Universal Tester made by the Shimadzu Corporation. The testing speed designated for these samples was 5.0 mm/min. This test revealed that the compressive strength of the macroporous material obtained in this invention can be well controlled within the scope of 1-16 MPa.

2.2. The Porosity of the Macroporous Materials

The Archimedes Method was used to carry out a test with a part of the samples mentioned above to determine their porosities, and a Scanning Electron Microscope (SEM) was used to observe their pore shapes and distribution. This test demonstrated that the porosity of the macroporous material obtained in this invention can be well controlled within a range of 40-80%.

2.3 Bioactivity Evaluation

A test of in vitro solution bioactivity was carried out with the macroporous materials obtained in the present invention, after being washed in de-ionized water and acetone successively, and then air dried afterwards. The solution applied was simulated body fluids (SBF). The ion and ionic group concentrations in this SBF are the same as those in human plasma. This SBF's composition is as below:

| | |
|---|---|
| NaCl: | 7.996 g/L |
| $NaHCO_3$: | 0.350 g/L |

-continued

| | |
|---|---|
| KCl: | 0.224 g/L |
| $K_2HPO_4 \cdot 3H_2O$: | 0.228 g/L |
| $MgCl_2 \cdot 6H_2O$: | 0.305 g/L |
| HCl: | 1 mol/L |
| $CaCl_2$: | 0.278 g/L |
| $Na_2SO_4$: | 0.071 g/L |
| $NH_2C(CH_2OH)_3$: | 6.057 g/L |

Figure 3:
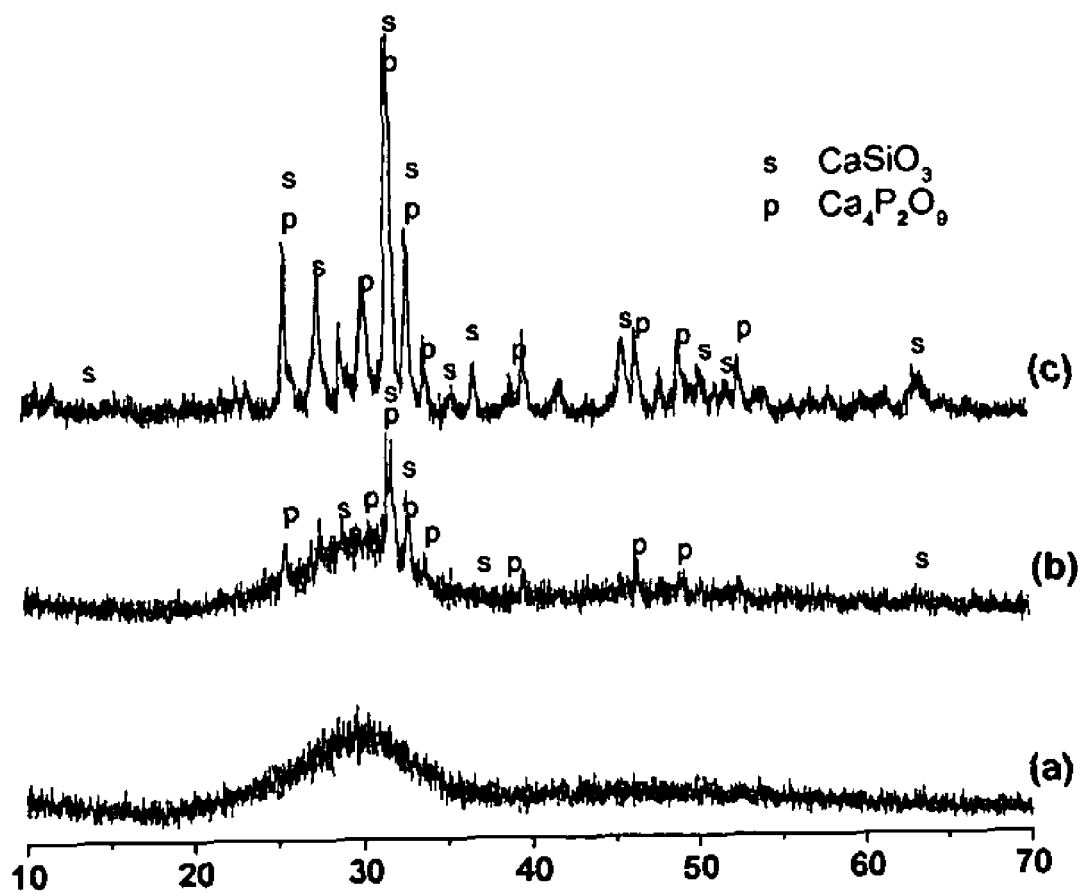
FIG. 3 shows XRD displays for the macroporous bioactive glass materials prepared under different temperatures; these illustrations show that different levels of crystallization of calcium silicate or calcium phosphate can be found on the surface of the materials prepared under different temperatures; (a) bioactive glass powder before sintering, (b) bioactive glass scaffolds prepared by sintering at 800° C., (c) bioactive glass scaffolds prepared by sintering at 850° C.
Figure 4A:
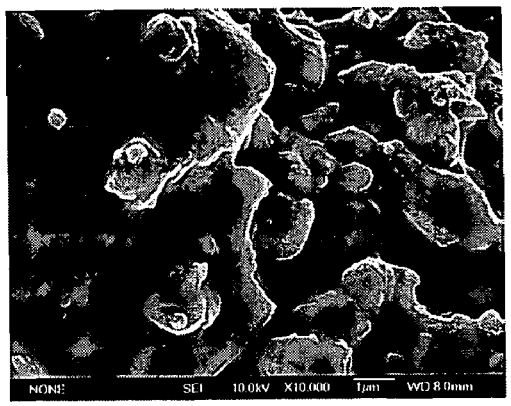
FIG. 4(A) is an SEM picture of the macroporous bioactive glass material of this invention before being immersed in SBF (i.e. simulated body fluids); 4(B) is an SEM picture of the material immersed SBF for 1 day; 4(C) is an SEM picture of the material when immersed in SBF for over 3 days; these pictures show that substantial hydroxyapatite crystalline can form on the surface of the material when immersed in SBF for 1 day.
Figure 4B:
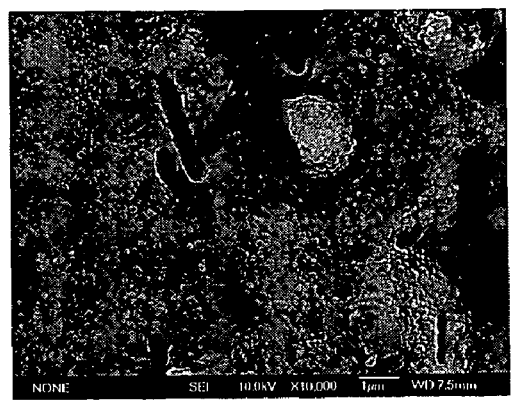
Figure 4C:
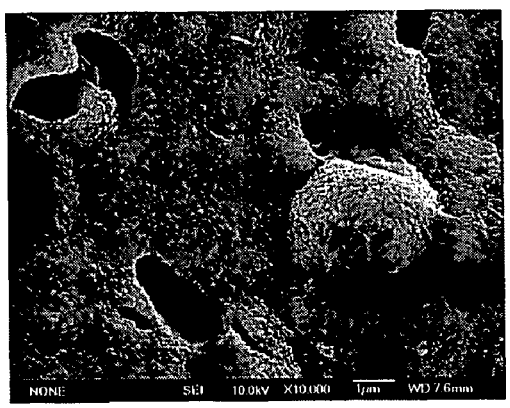
Figure 5:
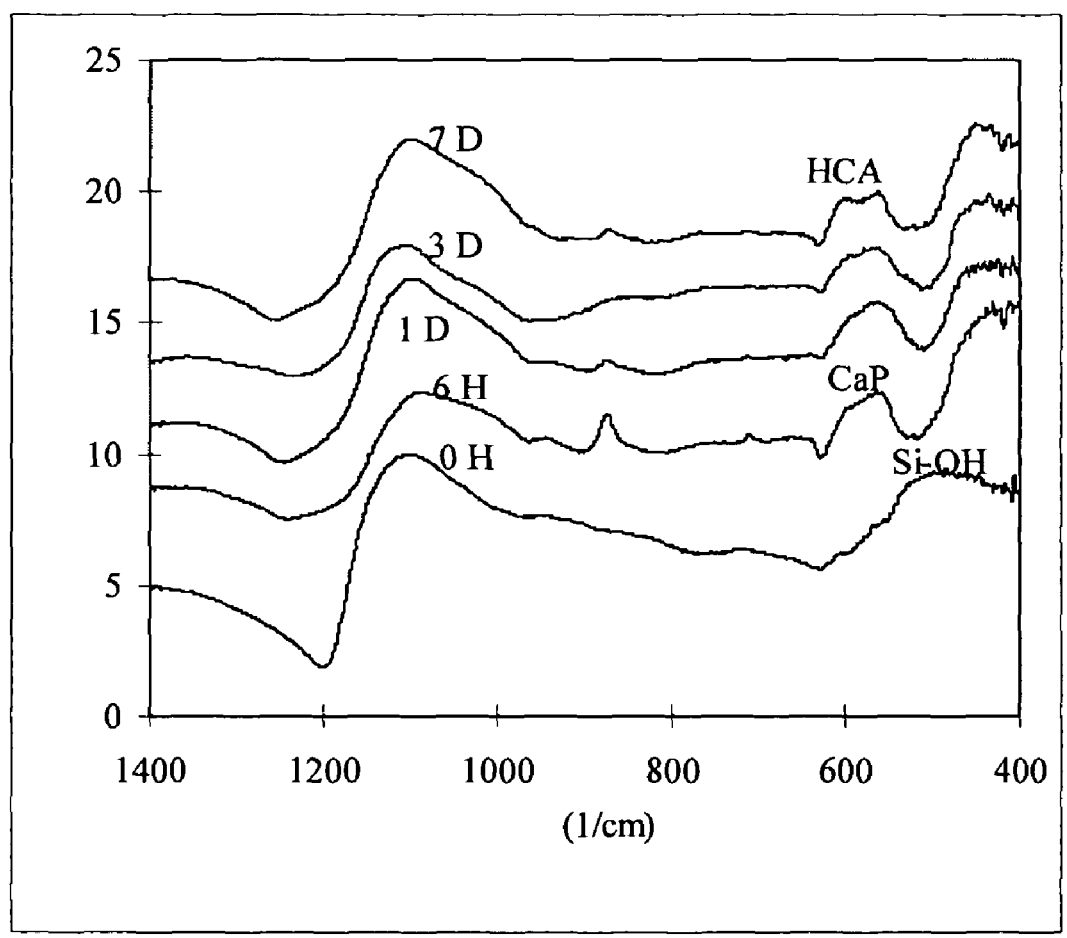
FIG. 5 is a Fourier Transform Infrared spectrometry (FTIR) spectra of the macroporous bioactive glass materials before being immersed in SBF, as well as after being immersed in SBF for 0 hours, 6 hours, 1 day, 3 days and 7 days respectively; the resulting analysis reveals that the hydroxylapatite peak can be observed when such material has been immersed in SBF for only 6 hours.

The test was carried out with macroporous material immersed in SBF in the following conditions: 0.15 g of macroporous material, 30.0 ml/day SBF, 37° C. in a temperature-controlled water-bath. After the macroporous material was immersed in SBF for a period of 1, 3 or 7 days respectively, samples were taken out and washed using ion water, and then underwent the SEM, Fourier Transform Infrared spectrometry (FTIR) and XRD tests. The respective results of the tests can be seen in FIGS. 3, 4 and 5. The relevant bioactivity experiment results have shown that the macroporous glass scaffold materials obtained in the present invention can induce the formation of bone-like hydroxyapatite on their surface, indicating ideal bioactivity of these materials.

2.4 Degradability Evaluation

A bioactivity experimental test was conducted on the macroporous materials in this invention after being washed in de-ionized water and acetone successively, and then dried. Evaluation of both degradation speed and degradability of the macroporous materials according to the content of $SiO_2$ substances that are released at different time points after the materials have been immersed in SBF was conducted. For example, where PEG is used as the pore forming agent, the macroporous bioactive glass scaffolds (porosity at 40%) obtained after the processes of dry pressing molding and calcination (temperature at 850° C.) exhibit a degradability of 10-20% when the scaffold has been immersed in SBF for 5 days.

IMPLEMENTATION EXAMPLE 1

The raw materials used in this example are the same as those described above.

Figure 2:
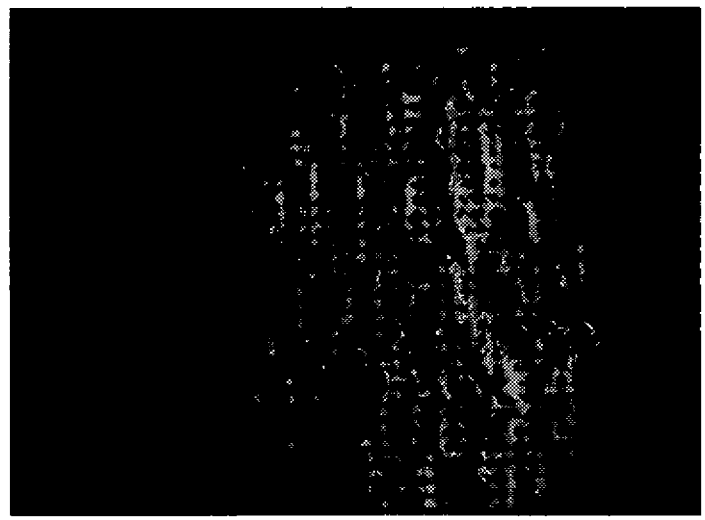
FIG. 2 is an optical microscope picture displaying cross-sections of the macroporous bioactive glass.

$SiO_2$, $Na_2CO_3$, $CaCO_3$ and $P_2O_5$ (all of analytical purity) are mixed proportionally, and the mixture is melted into homogenous fused masses at the temperature of 1420° C. and then cooled, crushed and sieved to obtain bioactive glass powder with a particle diameter ranging from 40-300 microns. The composition of the bioactive glass powder is expressed as CaO 24.5%, $SiO_2$ 45%, $Na_2O$ 24.5% and $P_2O_5$ 6%. Next, the bioactive glass powder (150-200 microns in granularity) is mixed with the polyethylene glycol powder (200-300 microns in granularity) at a mass percent of 60:40. Polyvinyl alcohol solution (6%), which serves as the adhesive, is added and the solution is mixed. The mixture is then dry-pressed under a pressure of 14 MPa, and the pellets of the macroporous materials are stripped from the mold. The pellets are first processed at 400° C. to remove organics, and then sintered at 850° C. for 2 hours to obtain the said macroporous materials with a compressive strength at approx. 1.25 MPa and a porosity at about 56%. The XRD indicates the existence of both the $Ca_4P_2O_9$ and $CaSiO_3$, as shown in FIG. 2(C).

Finally, the said macroporous materials are immersed in simulated body fluids (SBF) for periods of 6 hours and 1, 3, and 7 days respectively, and evaluated as to both bioactivity and resorbability/degradability. Results in FIGS. 4 and 5 demonstrate that the macroporous glass material of this invention has strong bioactivity, as a bone-like apatite layer is soon formed on the surface of such materials after they are immersed in SBF. After this material has been immersed in SBF for 5 days, its degradation rate can be up to a level of 14%, suggesting that the macroporous bioactive glass material in this invention has ideal degradability, and can therefore be expected to be successfully applied for the restoration of injured hard tissues and as the cell scaffold for in vitro culture of bone tissue.

IMPLEMENTATION EXAMPLE 2

$SiO_2$, $CaCO_3$, $Ca_3 (PO4)_2$, $MgCO_3$, $CaF_2$ (all of analytical purity) are mixed proportionally, melted into a homogenous fused masses at the temperature of 1450° C., and then cooled, crushed and sieved to obtain bioactive glass powder (particle diameter ranging from 40-300 microns). The composition of the bioactive glass powder is CaO 40.5%, $SiO_2$ 39.2%, MgO 4.5%, $P_2O_5$ 15.5% and $CaF_2$ 0.3%.

Next, the bioactive glass powder is blended with polyvinyl alcohol powder (300-600 microns in granularity) at a mass percent of 50:50 to obtain a solid mixture. An aqueous solution composed of 20% acrylamide, 2% N,N'-Methylene-bis-acrylamide and 8% polyacrylic acid is prepared, and 10 grams of the said solid mixture is blended with the aqueous solution at a volume percent (ratio) of 50:50, with several drops of ammonium persulfates (3% in mass percent) and several drops of N, N, N',N'-tetramethyl ethylene diamine (3% in mass percent) added and stirred to produce a slurry with fine fluidity, which is poured into molds for gelation-casting. The cross-linking reaction of monomers of the material is induced for 3 hours at 60° C. In this way, pellets of the macroporous material are obtained by stripping them from the mold after the gelation-casts have been dried at 100° C. for 12 hours. Subsequently, the pellets are processed at 400° C. to remove organics, and then sintered at 850° C. for 2 hours to produce the macroporous materials that feature a compressive strength at about 6.1 MPa and porosity at approx. 55%. This material demonstrated degradability is 78% (calculated based on the mass percent of Si releasing) after being immersed in Simulated Body Fluids for 3 days.

IMPLEMENTATION EXAMPLE 3

The raw materials and the preparation methods of the bioactive glass powder used in this example are the same as those in Implementation Example 2.

The bioactive glass powder (granularity at 150-200 microns) is blended with PEG powder (granularity at 200-300 microns) at the mass ratio of 40:60. Polyvinyl alcohol solution (concentration at 6%) is added to serve as the adhesive and mixed. This mixture is dry-pressed under a pressure of 14 MPa, and pellets of the macroporous materials are obtained by removal from the mold. The pellets are first processed at 400° C. to remove organics, and then sintered at 800° C. to obtain the said macroporous materials with a compressive strength at approx. 1.5 MPa and porosity at about 65%. After being immersed in Simulated Body Fluids for 3 days, the degradation rate of the macroporous glass material is 38% (calculated based on the mass percent of Si releasing).

It is understood and contemplated that equivalents and substitutions for certain elements and steps set forth above may be obvious to those skilled in the art, and therefore the true scope and definition of the invention is to be as set forth in the following claims.

We claim:

1. A method of manufacturing a resorbable, macroporous bioactive glass scaffold comprising the steps of:
   creating a mixture comprising by mass percent approximately 24-45% CaO, 34-50% $SiO_2$, 0-25% $Na_2O$, 5-17% $P_2O_5$, 0-5% MgO and 0-1% $CaF_2$;
   melting said mixture at a temperature ranging approximately from 1380° C. to 1480° C.;
   cooling, crushing and sieving said mixture to obtain glass powders having granularity of approximately 40-300 microns;
   adding into said glass powders by mass percent approximately 20-70% of at least one pore forming agent;
   adding approximately by volume percent 30-60% of an aqueous solution comprising by mass percent approximately 20% acrylamide monomers, 2% N,N'-methylene acrylamide cross-linking agents and 5-10% polyacrylic acid dispersant;
   adding by mass percent approximately 1-5% ammonium persulfates and 1-5% N, N,N',N'-tetramethyl ethylene diamine, and stirring to produce a well-proportioned slurry;
   pouring said slurry into dies and producing pellets by heating said slurry to a temperature of approximately 30° C. to 80° C. to induce cross-linking for a period of approximately 1-10 hours, then drying said pellets at a temperature of approximately 100° C.;
   heating said pellets to remove organics at a temperature of approximately 400° C.; and
   sintering said pellets for approximately 1-5 hours in temperatures ranging from approximately 750° C. to 900° C.

2. The method of claim 1, wherein the granularity of the said pore-forming agents is chosen to be between approximately 50-600 microns.

3. The method of claim 1, wherein said at least one pore forming agent is chosen from the group of pore forming agents consisting of polyethylene glycol, polyvinyl alcohol, paraffin and polystyrene-divinylbenzene.

* * * * *